(12) United States Patent
Trujillo et al.

(10) Patent No.: US 11,304,840 B2
(45) Date of Patent: Apr. 19, 2022

(54) UPPER BODY GARMENT WITH INTEGRATED INTERNAL POCKET

(71) Applicants: David Trujillo, Las Vegas, NV (US); Patricia Trujillo, Las Vegas, NV (US)

(72) Inventors: David Trujillo, Las Vegas, NV (US); Patricia Trujillo, Las Vegas, NV (US)

(*) Notice: Subject to any disclaimer, the term of this patent is extended or adjusted under 35 U.S.C. 154(b) by 283 days.

(21) Appl. No.: 16/033,470

(22) Filed: Jul. 12, 2018

(65) Prior Publication Data
US 2019/0117440 A1 Apr. 25, 2019

Related U.S. Application Data

(60) Provisional application No. 62/576,273, filed on Oct. 24, 2017.

(51) Int. Cl.
*A61F 5/37* (2006.01)
*A41B 1/10* (2006.01)
*A41D 27/20* (2006.01)
*A41D 13/12* (2006.01)

(52) U.S. Cl.
CPC .............. *A61F 5/3746* (2013.01); *A41B 1/10* (2013.01); *A41D 13/1245* (2013.01); *A41D 27/20* (2013.01); *A41B 2300/32* (2013.01); *A41B 2300/324* (2013.01); *A41B 2400/32* (2013.01)

(58) Field of Classification Search
CPC ...... A61F 5/3723; A61F 5/373; A61F 5/3738; A61F 5/3746; A41B 1/10; A41B 2300/32; A41B 2300/324; A41B 2400/32; A41D 13/1236; A41D 13/1245; A41D 27/20; A41D 27/204; A41D 27/205; A47G 9/0223
See application file for complete search history.

(56) References Cited

U.S. PATENT DOCUMENTS

| | | | | |
|---|---|---|---|---|
| 5,564,123 A * | 10/1996 | Grassick | ............ | A41D 13/1245 2/114 |
| 6,216,271 B1 * | 4/2001 | Chen | ............ | A41D 13/1245 2/114 |
| 6,240,563 B1 | 6/2001 | Niedermeyer | | |
| 6,595,936 B1 * | 7/2003 | Oladipo | ............ | A61F 5/3746 602/20 |
| 9,788,671 B1 * | 10/2017 | Wuerz | ............ | A47G 9/0223 |
| 2009/0106872 A1 | 4/2009 | Collins | | |
| 2009/0205102 A1 * | 8/2009 | Anderson | ............ | A41D 3/00 2/85 |
| 2015/0216712 A1 * | 8/2015 | Wilson, Jr. | ............ | A61F 5/3738 602/4 |
| 2016/0113328 A1 * | 4/2016 | Sacks | ............ | A41D 13/1245 2/115 |
| 2016/0128391 A1 | 5/2016 | Moore | | |
| 2016/0150838 A1 * | 6/2016 | Lee | ............ | A61J 15/0053 2/113 |

(Continued)

*Primary Examiner* — Camtu T Nguyen
(74) *Attorney, Agent, or Firm* — Boudwin Intellectual Property; Daniel Boudwin

(57) ABSTRACT

An upper body garment with an integrated internal pocket. The upper body garment includes a shirt member that has a front portion and a rear portion with a pair of side openings. A plurality of fasteners is embedded along the side openings that allow a wearer to close the side openings. The fasteners attach the front portion to the rear portion. The internal surface of the front portion has an integrated pocket to receive a forearm of the wearer.

9 Claims, 4 Drawing Sheets

(56) References Cited

U.S. PATENT DOCUMENTS

2016/0309811 A1\* 10/2016 Tong ................... A41D 13/1245
2016/0366953 A1\* 12/2016 Watts .................. A41D 13/0058
2017/0095366 A1\*  4/2017 Thrasher ............... A61F 5/3746

\* cited by examiner

UPPER BODY GARMENT WITH INTEGRATED INTERNAL POCKET

CROSS REFERENCE TO RELATED APPLICATIONS

This application claims the benefit of U.S. Provisional Application No. 62/576,273 filed on Oct. 24, 2017. The above identified patent application is herein incorporated by reference in its entirety to provide continuity of disclosure.

BACKGROUND OF THE INVENTION

The present invention relates to an upper body garment with an integrated internal pocket. When an individual suffers an injury that requires stabilization of his or her arm or shoulder, he or she may be directed by a medical professional to use a device such as an arm sling. Furthermore, injuries that require this type of treatment typically cause a loss of range of motion. Particularly, it may be difficult for an individual to put a shirt on himself or herself.

Even though arm slings are assistive in the treatment of arm or shoulder ailments, wherein stabilization of the shoulder is a treatment, they do not assist a user in putting on a shirt. An individual may indeed subject himself or herself to additional pain and discomfort in putting on a traditional shirt and may even cause more damage to be done, extending the treatment time of the arm or shoulder ailment. Therefore, there is a need for a garment that provides the advantages of a sling, wherein a shoulder joint may be stabilized as part of a medical treatment, while minimizing the detriments, such as the pain and discomfort of putting a shirt and a sling on.

SUMMARY OF THE INVENTION

In view of the foregoing disadvantages inherent in the known types of shoulder stabilization medical apparatuses now present in the known art, the present invention provides a garment with an internal, integrated pocket wherein the same can be utilized for providing convenience for the user when stabilizing a shoulder joint to treat an arm or shoulder ailment.

The present system comprises a shirt member having a front portion and a rear portion. The shirt member defines an upper opening configured to receive the head of a wearer therein. Furthermore, the shirt member defines a pair of side openings to receive at least one arm of a wearer therethrough, as well as a lower opening configured to receive a torso of a wearer therethrough. A plurality of fasteners is disposed along a perimeter of each of the front portion and rear portion. The plurality of fasteners is adapted to secure the front portion to the rear portion. An integrated pocket is disposed on an internal surface of the front portion.

An additional object of the present invention is to provide a plurality of fasteners that is a plurality of snap clasp fasteners to provide convenience to a wearer in putting the garment on.

Another object of the present invention is to provide a plurality of fasteners that is a plurality of hook and loop fasteners to provide convenience to the wearer in putting the garment on.

Yet another object of the present invention is to provide an integrated pocket that is sized to receive a forearm of a wearer therein to provide comfort and shoulder stabilization to the wearer.

A further object of the present invention is to provide an external pocket on the front portion to provide convenience to the wearer.

An additional object of the present invention is to provide a garment wherein the front portion and the rear portion are sewn together at a top end thereof, so as to provide structural stability to the garment.

Yet another object of the present invention is to provide a garment wherein a closeable slit extends toward a base end of the front portion from the upper opening, such as to provide additional comfort to a user.

A further object of the present invention is to provide a second integrated pocket disposed on an internal surface of the rear portion, so as to allow the wearer to use the garment to stabilize either of a wearer's pair of shoulder joints.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
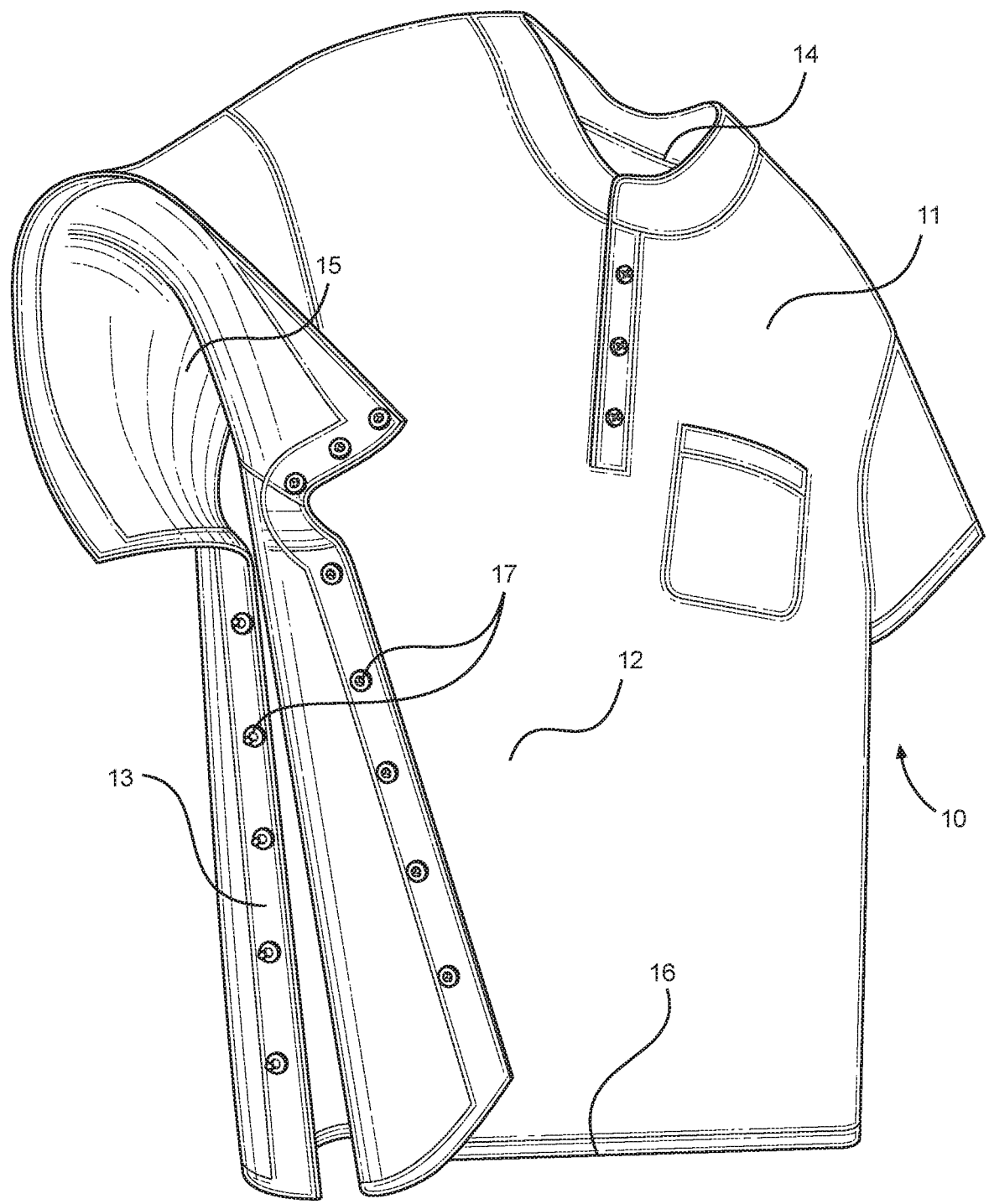
FIG. 1 shows a perspective view of an embodiment of the upper body garment with integrated internal pocket.

Reference is made herein to the attached drawings. Like reference numerals are used throughout the drawings to depict like or similar elements of the upper body garment. The figures are intended for representative purposes only and should not be considered to be limiting in any respect.

Referring now to FIG. 1, there is shown a perspective view of an embodiment of the upper body garment with integrated internal pocket. The upper body garment 10 comprises a shirt member 11 having a front portion 12 and a rear portion 13. Furthermore, the shirt member 11 defines an upper opening 14. The upper opening 14 is configured to receive a head of a wearer therethrough. In the shown embodiment, the upper opening 14 comprises a double layer of fabric, such as to provide comfort to a neck of the wearer while also providing increased durability to the upper opening 14.

The shirt member 11 further defines a pair of side openings 15. The pair of side openings 15 is configured to receive either of a pair of arms of the wearer therethrough. Additionally, the shirt member 11 defines a lower opening 16. The lower opening 16 is configured to receive the torso of the wearer therethrough.

A plurality of fasteners 17 is disposed along at least one perimeter section of each of the front portion 12 and the rear portion 13. In the illustrated embodiment, the perimeter section extends between each of the pair of side openings 15 to opposing sides of the lower opening 16. The plurality of fasteners 17 is configured to fasten the front portion 12 of the shirt member 11 to the rear portion 13. When fastened, the plurality of fasteners 17 transforms the upper body garment 10 into a wearable configuration. In the shown embodiment, the plurality of fasteners 17 is a plurality of snap clasp fasteners. In another embodiment, the plurality of fasteners is a plurality of hook and loop fasteners.

In one embodiment, the front portion 12 and the rear portion 13 are affixed at a top end of the shirt member 11. Under this embodiment, the attachment of the front portion 12 and the rear portion 13 will provide additional stability to the upper body garment 10 such that the wearer will more easily be able to put on and remove the upper body garment 10. Rather than attaching the front portion 12 to the rear portion 13 about an entire perimeter thereof, the user can instead rest the top end on their shoulders while the plurality of fasteners 17 are fastened.

Figure 2:
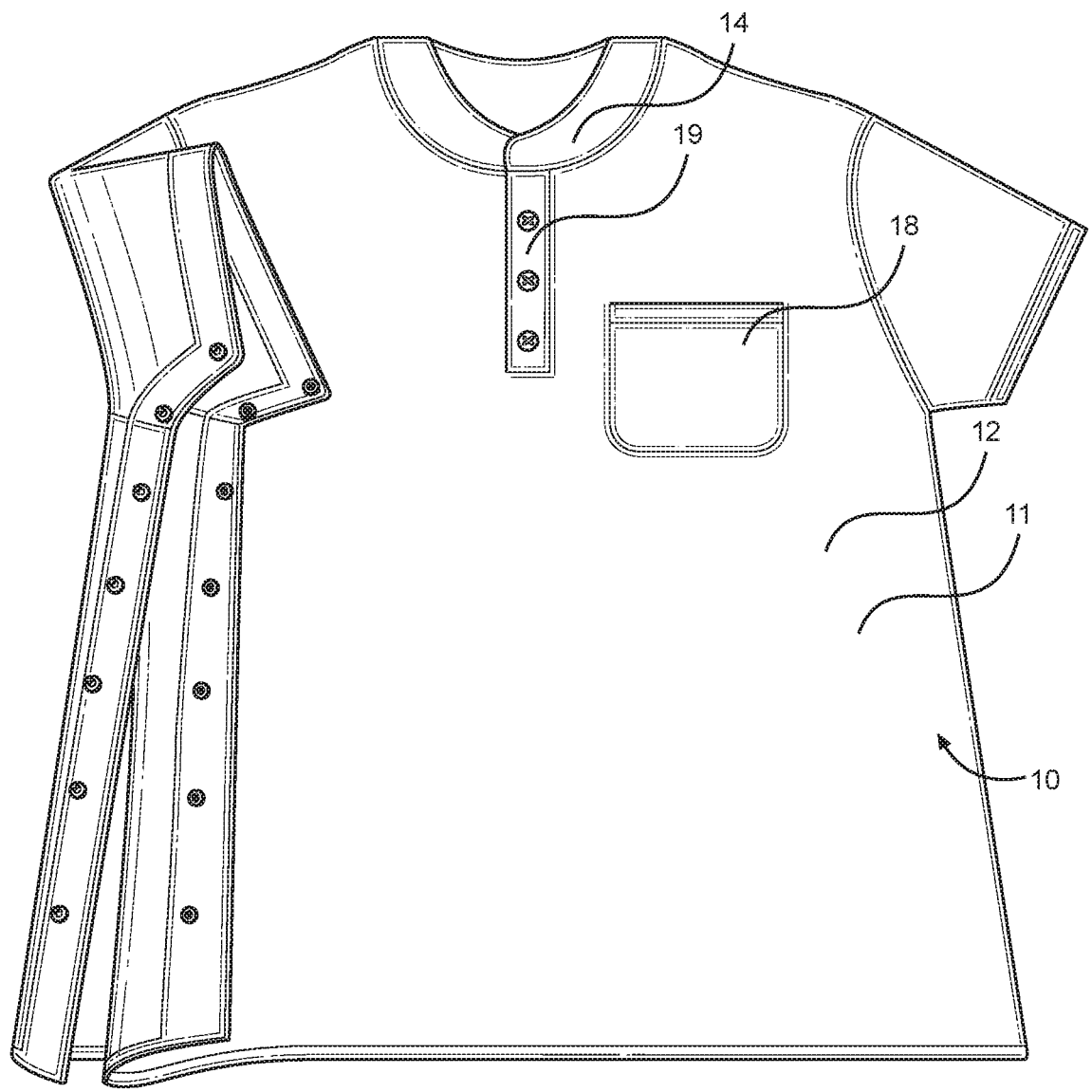
FIG. 2 shows a front view of an embodiment of the upper body garment with integrated internal pocket.

Referring now to FIG. 2, there is shown a front view of an embodiment of the upper body garment with integrated internal pocket. In the shown embodiment, the shirt member 11 further comprises an external pocket 18 affixed on an external surface of the front portion 12. The external pocket 18 is configured to provide convenience to the wearer wherein the external pocket 18 is adapted to house an object therein.

In the illustrated embodiment, the upper body garment 10 comprises a slit 19. The slit 19 extends toward a base end of the front portion 12 of the shirt member 11 from the upper opening 14. In the shown embodiment, a plurality of buttons is disposed on the slit 19 such as to allow closure of the slit 19.

Figure 3:
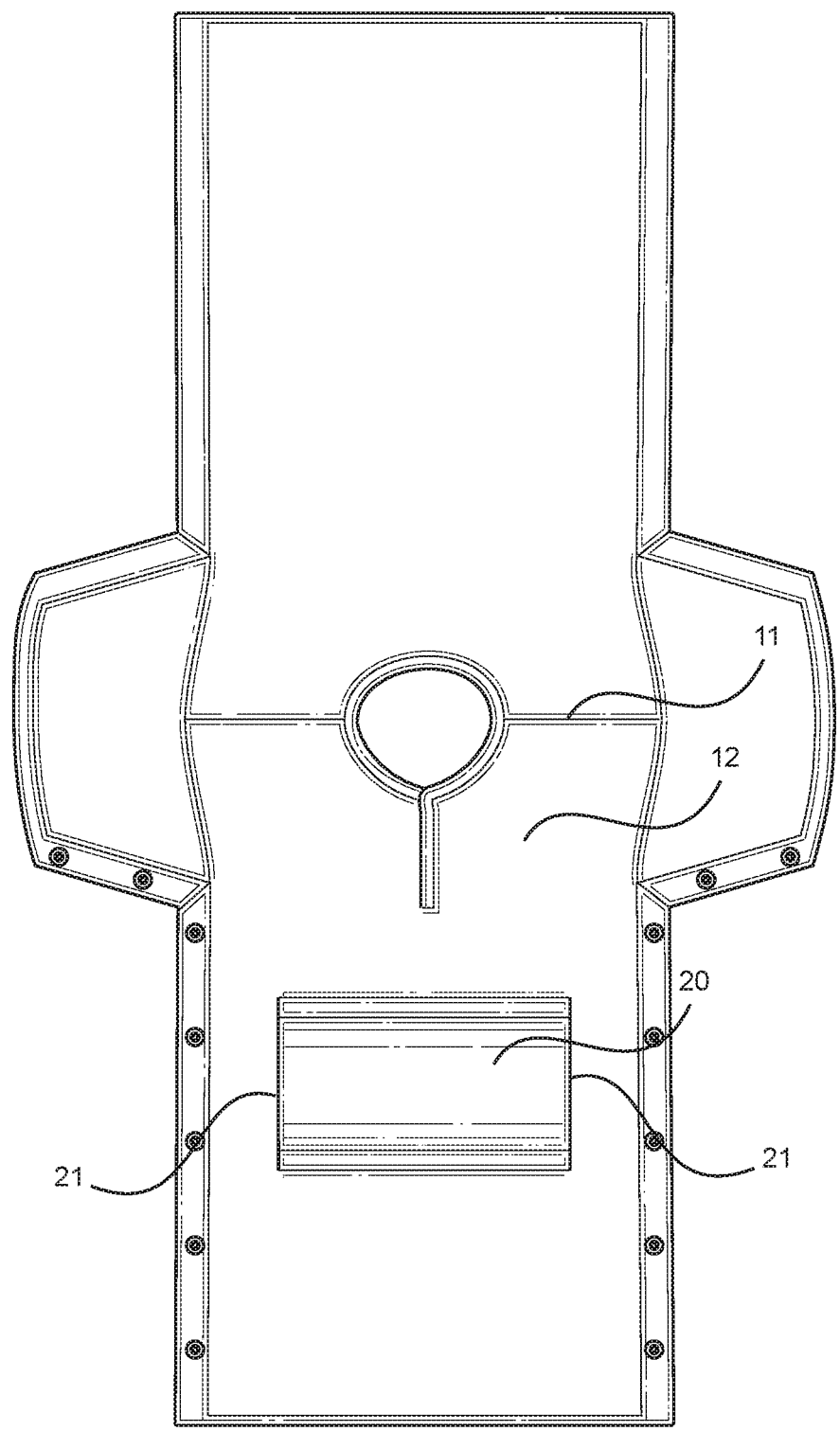
FIG. 3 shows an internal view of an embodiment of the upper body garment with integrated internal pocket.

Referring now to FIG. 3, there is shown an internal view of an embodiment of the upper body garment with integrated internal pocket. An integrated pocket 20 is disposed on an interior surface of the front portion 12 of the shirt member 11. In one embodiment, the integrated pocket 20 is open on each of a pair of opposing end portions 21 so as to provide comfort to the wearer. In this way, the integrated pocket 20 provides support to the user's shoulder joint when the arm of the user is received therein. In some embodiments, the integrated pocket 20 includes a padded internal surface, such that the user is provided additional comfort during use.

Figure 4:
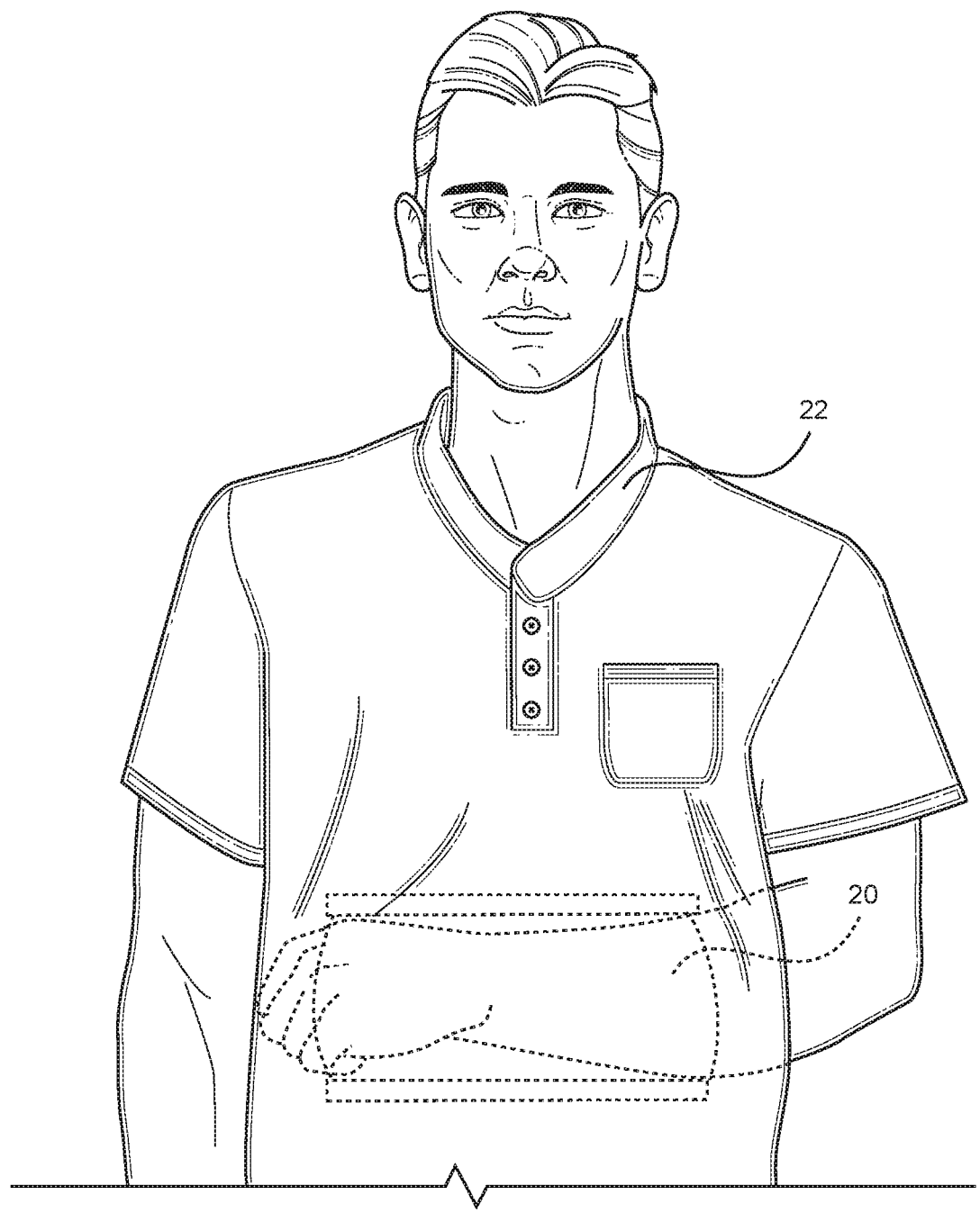
FIG. 4 shows a perspective view of an embodiment of the upper body garment with integrated internal pocket in use.

Referring now to FIG. 4, there is shown a perspective view of an embodiment of the upper body garment with integrated internal pocket in use. As shown in the illustrated embodiment, the integrated pocket 20 is configured to receive a forearm of a wearer therein. In another embodiment, a second integrated pocket is disposed on an internal surface of the rear portion, such that the wearer can rotate the upper body around a vertical axis to provide a pocket for an opposite arm. Under this embodiment, the upper body garment is changeable between a position providing support to a right arm of a user and a position providing support to a left arm of a user.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An upper body garment with integrated pocket, comprising:
    a shirt member having a front portion and a rear portion defining an upper opening, a pair of side openings, and a lower opening;
    a plurality of fasteners disposed along a pair of perimeter sections of each of the front portion and the rear portion;
    the plurality of fasteners configured to secure the front portion to the rear portion;
    the rear portion releasably secured to the front portion along the pair of perimeter sections and at the lower opening;
    the integrated pocket disposed on an internal surface of the front portion;
    the integrated pocket defining a pair of openings on opposing ends of the integrated pocket;
    the pair of openings accessible on the internal surface of the front portion via the pair of perimeter sections.

2. The upper body garment with integrated pocket of claim 1, wherein the plurality of fasteners is a plurality of snap clasp fasteners.

3. The upper body garment with integrated pocket of claim 1, wherein the plurality of fasteners is a plurality of hook and loop fasteners.

4. The upper body garment with integrated pocket of claim 1, wherein the integrated pocket is adapted to receive a forearm of a wearer therein.

5. The upper body garment with integrated pocket of claim 1, wherein a pocket is disposed on an external surface of the front portion.

6. The upper body garment with integrated pocket of claim 1, wherein the front portion and the rear portion are affixed along a top end thereof.

7. The upper body garment with integrated pocket of claim 1, wherein the upper opening further comprises a double layer of a fabric material therearound.

8. The upper body garment with integrated pocket of claim 1, further comprising a slit comprising a plurality of buttons, the slit disposed on the front portion of the shirt member extending downward from the upper opening.

9. The upper body garment with integrated pocket of claim 1, wherein the pair of perimeter sections extend between the pair of side openings to opposing sides of the lower opening.

* * * * *